US00PP32402P2

(12) United States Plant Patent
Arts

(10) Patent No.: US PP32,402 P2
(45) Date of Patent: Oct. 27, 2020

(54) ***HYDRANGEA* PLANT NAMED 'H218926'**

(50) Latin Name: *Hydrangea macrophylla*
Varietal Denomination: H218926

(71) Applicant: HYDRANGEA BREEDERS ASSOCIATION B.V., De Kwakel (NL)

(72) Inventor: Niels Arts, Aalsmeer (NL)

(73) Assignee: Hydrangea Breeders Association B.V., De Kwakel (NL)

( * ) Notice: Subject to any disclaimer, the term of this patent is extended or adjusted under 35 U.S.C. 154(b) by 0 days.

(21) Appl. No.: 16/602,115

(22) Filed: Aug. 7, 2019

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Hydrangea* plant named 'H218926', characterized by its upright and uniformly mounded plant habit; vigorous growth habit and rapid growth rate; freely branching habit with strong, thick and sturdy stems; freely and uniformly flowering habit; large mophead-type inflorescences with numerous white and light red purple bi-colored sterile flowers; and good postproduction longevity.

3 Drawing Sheets

Botanical designation: *Hydrangea macrophylla.*
Cultivar denomination: 'H218926'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'H218926'.

The new *Hydrangea* plant is a product of a planned breeding program conducted by the Inventor in De Kwakel, The Netherlands and Lengerich, Germany. The objective of the breeding program was to create new strong and freely-branching *Hydrangea* plants with strong sturdy stems, uniform flowering habit, large inflorescences with numerous showy sterile flowers, attractive sterile flower color and good postproduction longevity.

The new *Hydrangea* plant originated from a cross-pollination made by the Inventor in March, 2010 in De Kwakel, The Netherlands, of a proprietary selection of *Hydrangea macrophylla* identified as code number 07-0132-150, not patented, as the female, or seed, parent with a proprietary selection of *Hydrangea macrophylla* identified as code number 05-0109-080, not patented, as the male, or pollen, parent. The new *Hydrangea* plant was discovered and selected by the Inventor as a single flowering plant from within the progeny of the stated cross-pollination in a controlled greenhouse environment in Lengerich, Germany in March, 2011.

Asexual reproduction of the new *Hydrangea* plant by vegetative tip cuttings in a controlled environment in De Kwakel, The Netherlands since April, 2011 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'H218926'. These characteristics in combination distinguish 'H218926' as a new and distinct *Hydrangea* plant:

1. Upright and uniformly mounded plant habit.
2. Vigorous growth habit and rapid growth rate.
3. Freely branching habit with strong, thick and sturdy stems.
4. Freely and uniformly flowering habit.
5. Large mophead-type inflorescences with numerous white and light red purple bi-colored sterile flowers.
6. Good postproduction longevity.

Plants of the new *Hydrangea* can be compared to plants of the female parent selection. Plants of the new *Hydrangea* differ primarily from plants of the female parent selection in sterile flower color as plants of the new *Hydrangea* have white and light red purple bi-colored sterile flowers whereas plants of the female parent selection have white-colored sterile flowers.

Plants of the new *Hydrangea* can be compared to plants of the male parent selection. Plants of the new *Hydrangea* differ primarily from plants of the male parent selection in sterile flower color as plants of the new *Hydrangea* have white and light red purple bi-colored sterile flowers whereas plants of the male parent selection have light red purple-colored sterile flowers.

Plants of the new *Hydrangea* can be compared to plants of the *Hydrangea macrophylla* 'H213902', disclosed in U.S. Plant Pat. No. 26,219. In side-by-side comparisons, plants of the new *Hydrangea* differ primarily from plants of 'H213902' in the following characteristics:

1. Plants of the new *Hydrangea* are not as vigorous as plants of 'H213902'.

2. Plants of the new *Hydrangea* have larger leaves than plants of 'H213902'.
3. Plants of the new *Hydrangea* have smaller panicles than plants of 'H213902'.
4. Plants of the new *Hydrangea* have more fertile and sterile flowers per panicle than plants of 'H213902'.
5. Plants of the new *Hydrangea* have white and light red purple bi-colored sterile flowers whereas plants of 'H213902' have white-colored sterile flowers.
6. Plants of the new *Hydrangea* can be successfully "blued" with aluminum sulfate whereas plants of 'H213902' treated with aluminum sulfate have not been observed to show a discernable flower color change.

Plants of the new *Hydrangea* can also be compared to plants of the *Hydrangea macrophylla* 'HBA215908', disclosed in U.S. Plant Pat. No. 29,170. In side-by-side comparisons, plants of the new *Hydrangea* differ primarily from plants of 'HBA215908' in the following characteristics:

1. Plants of the new *Hydrangea* have more slender stems than plants of 'HBA215908'.
2. Plants of the new *Hydrangea* have smaller panicles than plants of 'HBA215908'.
3. Sterile flowers of plants of the new *Hydrangea* are smaller than sterile flowers of plants of 'HBA215908'.
4. Plants of the new *Hydrangea* have white and light red purple bi-colored sterile flowers whereas plants of 'HBA215908' have red purple-colored sterile flowers.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'H218926'.

The photograph on the second sheet is a close-up view of a typical inflorescence of 'H218926'.

The photograph on the third sheet is a side perspective view of a typical flowering plant of 'H218926' that has been "blued" (left) that is, treated with aluminum sulfate, and a side perspective view of a typical flowering plant of 'H218926' that has not been "blued" (right) that is, not treated with aluminum sulfate.

DETAILED BOTANICAL DESCRIPTION

Plants used in the aforementioned photographs and in the following description were grown during the early spring to summer in 13-cm containers in a glass-covered greenhouse in De Kwakel, The Netherlands and under cultural practices typical of commercial *Hydrangea* production. During the production of the plants, day and night temperatures averaged 17° C. Plants of the new *Hydrangea* were ten months old when the photographs and description were taken. Plants of the new *Hydrangea* can be successfully treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'H218926'.

Parentage:

*Female, or seed, parent*.—Proprietary selection of *Hydrangea macrophylla* identified as code number 07-0132-150, not patented.

*Male, or pollen, parent*.—Proprietary selection of *Hydrangea macrophylla* identified as code number 05-0109-080, not patented.

Propagation:

*Type cutting*.—By vegetative tip cuttings.

*Time to initiate roots, summer*.—About two weeks at temperatures about 23° C.

*Time to initiate roots, winter*.—About 18 days at temperatures about 20° C.

*Time to produce a rooted young plant, summer*.—About four weeks at temperatures about 23° C.

*Time to produce a rooted young plant, winter*.—About five weeks at temperatures about 20° C.

*Root description*.—Thick; typically whitish brown in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Upright and uniformly mounded plant habit; strong and sturdy stems; rapid growth rate and vigorous growth habit.

*Plant height*.—About 30 cm to 40 cm.

*Plant diameter or area of spread*.—About 50 cm.

Lateral branch description:

*Branching habit*.—Freely branching habit; when pinched, about seven to nine lateral branches develop per plant.

*Length*.—About 25 cm to 30 cm.

*Diameter*.—About 6 mm to 8 mm.

*Internode length*.—About 3 cm to 4 cm.

*Texture*.—Smooth, glabrous; fully developed, woody.

*Aspect*.—Upright to about 20° from vertical.

*Strength*.—Strong, sturdy.

*Color*.—When developing: Close to 144C; at internodes, close to 187C; lenticels, close to 186B. Developed: Close to 144C; at the internodes, close to 187C; when woody, close to 177C; lenticels, close to 186B.

Leaf description:

*Arrangement*.—Opposite, simple.

*Length*.—About 12 cm to 15 cm.

*Width*.—About 10 cm to 11 cm.

*Shape*.—Ovate.

*Apex*.—Acute.

*Base*.—Obtuse.

*Margin*.—Dentate.

*Texture, upper surface*.—Smooth to rugose, glabrous.

*Texture, lower surface*.—Rugose, glabrous.

*Venation pattern*.—Pinnate.

*Color*.—Developing leaves, upper surface: Close to 147A. Developing leaves, lower surface: Close to 147C. Fully expanded leaves, upper surface: Close to 147A; venation, close to 146B. Fully expanded leaves, lower surface: Close to 146B; venation, close to 139D.

*Petioles*.—Length: About 3 cm to 4 cm. Diameter: About 3 mm to 4 mm. Texture, upper and lower surfaces: Smooth, glabrous. Color, upper and lower surfaces: Close to 145B.

Flower description:

*Flower type and habit*.—Showy sterile flowers and small inconspicuous fertile flowers arranged on large mophead-type terminal panicles; panicles globular in shape; flowers face upright to outwardly depending on their position in the inflorescence.

*Fragrance*.—None detected.

*Natural flowering season*.—Plants begin flowering about three months after planting; flowering begins in the early summer and is continuous throughout the summer in Northern Europe.

*Flower longevity*.—Fertile flowers last about one month on the plant, fertile flowers not persistent; sterile flowers last about four months on the plant, sterile flowers persistent.

*Quantity of flowers*.—Freely flowering habit; about 40 to 45 fertile flowers per panicle and about 130 to 150 sterile flowers per panicle.

*Panicle height*.—About 10 cm to 13 cm.

*Panicle diameter*.—About 16 cm to 18 cm.

*Fertile flower buds*.—Length: About 3 mm. Diameter: About 3 mm. Shape: Spherical. Color: Close to 69C.

*Sterile flower buds*.—Length: About 2 mm to 3 mm. Diameter: About 2 mm. Shape: Spherical. Color: Close to 69C.

*Fertile flower diameter*.—About 3 mm to 4 mm.

*Fertile flower depth* (*height*).—About 3 mm.

*Sterile flower diameter*.—About 4 cm to 5 cm.

*Sterile flower depth* (*height*).—About 2 cm.

*Petals, fertile flowers*.—Quantity and arrangement: Five in a single whorl. Length: About 3 mm. Width: About 2 mm. Shape: Ovate. Apex: Acute. Base: Attenuate. Margin: Entire. Texture, upper and lower surfaces: Smooth, glabrous. Color: When opening, upper and lower surfaces: Close to 145D. Fully opened, upper surface: Close to N155B with irregular segments, close to 63C; color does not change with development. Fully opened, lower surface: Close to 69D; color does not change with development.

*Petals, sterile flowers*.—Quantity and arrangement: Four in a single whorl. Length: About 2 mm. Width: About 1.5 mm. Shape: Ovate. Apex: Acute. Base: Obtuse. Margin: Entire. Texture, upper and lower surfaces: Smooth, glabrous. Color: When opening, upper and lower surfaces: Close to 69C. Fully opened, upper and lower surfaces: Close to 69D; color does not change with development.

*Sepals, fertile flowers*.—Quantity and arrangement: Five in a single whorl. Length: About 1 mm to 2 mm. Width: About 1 mm. Shape: Ovate. Apex: Acute. Base: Obtuse. Margin: Entire. Texture, upper and lower surfaces: Smooth, glabrous. Color: When opening, upper and lower surfaces: Close to 145B. Fully opened, upper and lower surfaces: Close to 145D; color does not change with development.

*Sepals, sterile flowers*.—Quantity and arrangement: Four in a single whorl; imbricate. Length: About 2 cm to 2.5 cm. Width: About 2.2 cm to 2.7 cm. Shape: Deltoid to rhomboidal. Apex: Obtuse. Base: Cuneate to obtuse. Margin: Entire to slightly dentate. Texture, upper and lower surfaces: Smooth, glabrous. Color: When opening, upper surface: Close to 145B to 145D. When opening, lower surface: Close to 145C. Fully opened, upper surface: Close to NN155C with random and irregular sectors, stripes and spots, close to 63C to 63D; with development, color becoming closer to NN155B with random and irregular sectors, stripes and spots, close to 63D and 145C; when "blued", color becoming closer to NN155C with random and irregular sectors, stripes and spots, close to 98B to 98C. Fully opened, lower surface: Close to NN155B with random and irregular sectors, stripes and spots, close to 63D; color does not change with development.

*Pedicels, fertile flowers*.—Length: About 5 mm to 8 mm. Diameter: About 1.5 mm to 2 mm. Strength: Strong. Aspect: Mostly upright. Texture: Smooth, glabrous. Color: Close to 69D.

*Pedicels, sterile flowers*.—Length: About 2 cm to 3 cm. Diameter: About 2 mm. Strength: Strong. Aspect: Erect to about 45° from vertical. Texture: Smooth, glabrous. Color: Close to N155B.

*Reproductive organs, fertile flowers*.—Stamens: Quantity per flower: Eight. Filament length: About 3 mm. Filament color: Close to NN155B. Anther length: About 1 mm. Anther shape: Conical. Anther color: Close to 155B. Pollen amount: Abundant. Pollen color: Close to 155D. Pistils: Pistil quantity per flower: Three. Pistil length: About 3 mm to 4 mm. Stigma shape: Oval. Stigma color: Close to NN155B. Style length: About 1 mm to 2 mm. Style color: Close to NN155B. Ovary color: Close to NN155B.

*Reproductive organs, sterile flowers*.—Stamens: Quantity per flower: About six to eight. Filament length: About 3 mm. Filament color: Close to NN155B. Anther length: About 1 mm. Anther shape: Conical. Anther color: Close to 155B. Pollen amount: Moderate. Pollen color: Close to 155B. Pistils: Pistil quantity per flower: Three. Pistil length: About 3 mm to 4 mm. Stigma shape: Oval. Stigma color: Close to NN155B. Style length: About 1 mm to 2 mm. Style color: Close to NN155B. Ovary color: Close to NN155B.

*Seeds, only produced by fertile flowers*.—Quantity per fertile flower: About 20 to 30. Length: About 0.5 mm. Diameter: About 0.1 mm. Color: Close to 200C.

Pathogen & pest resistance: Under commercial production conditions, plants of the new *Hydrangea* have not been observed to be resistant to pathogens and pests common to *Hydrangea* plants to date.

Temperature tolerance: Plants of the new *Hydrangea* have been shown to be tolerant to temperatures ranging from about 3° C. to about 38° C.

It is claimed:

1. A new and distinct *Hydrangea* plant named 'H218926' as illustrated and described.

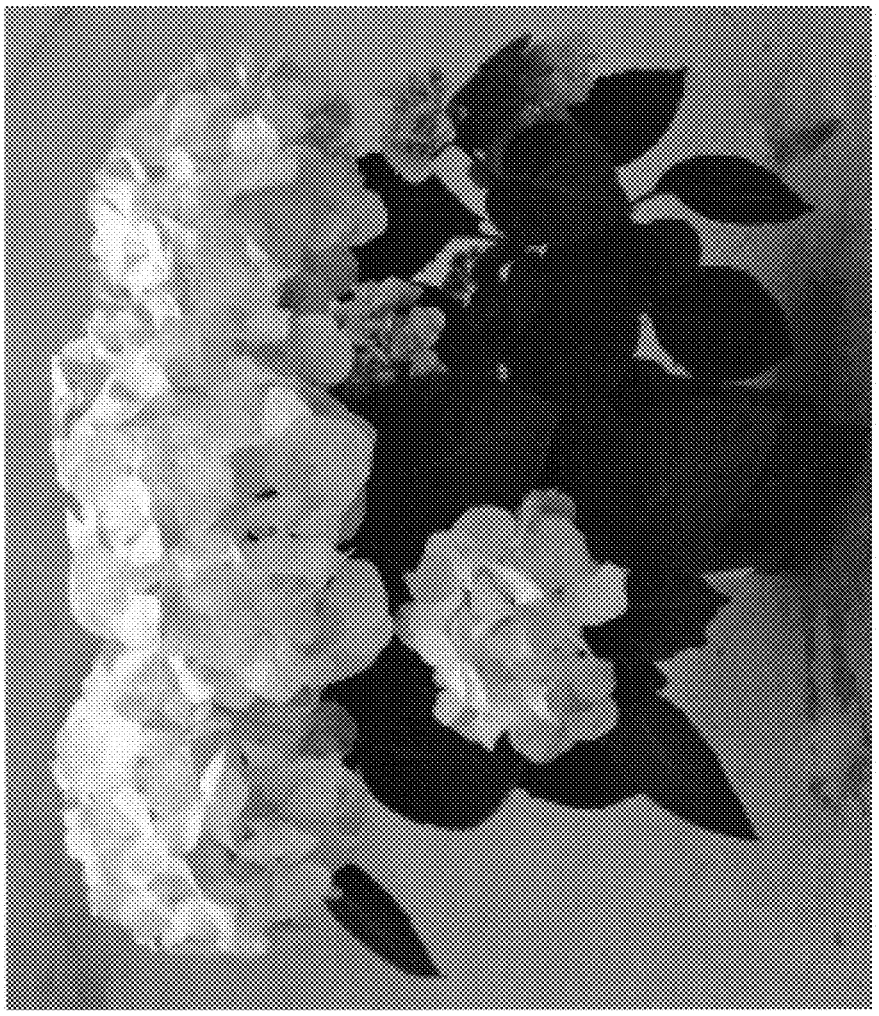

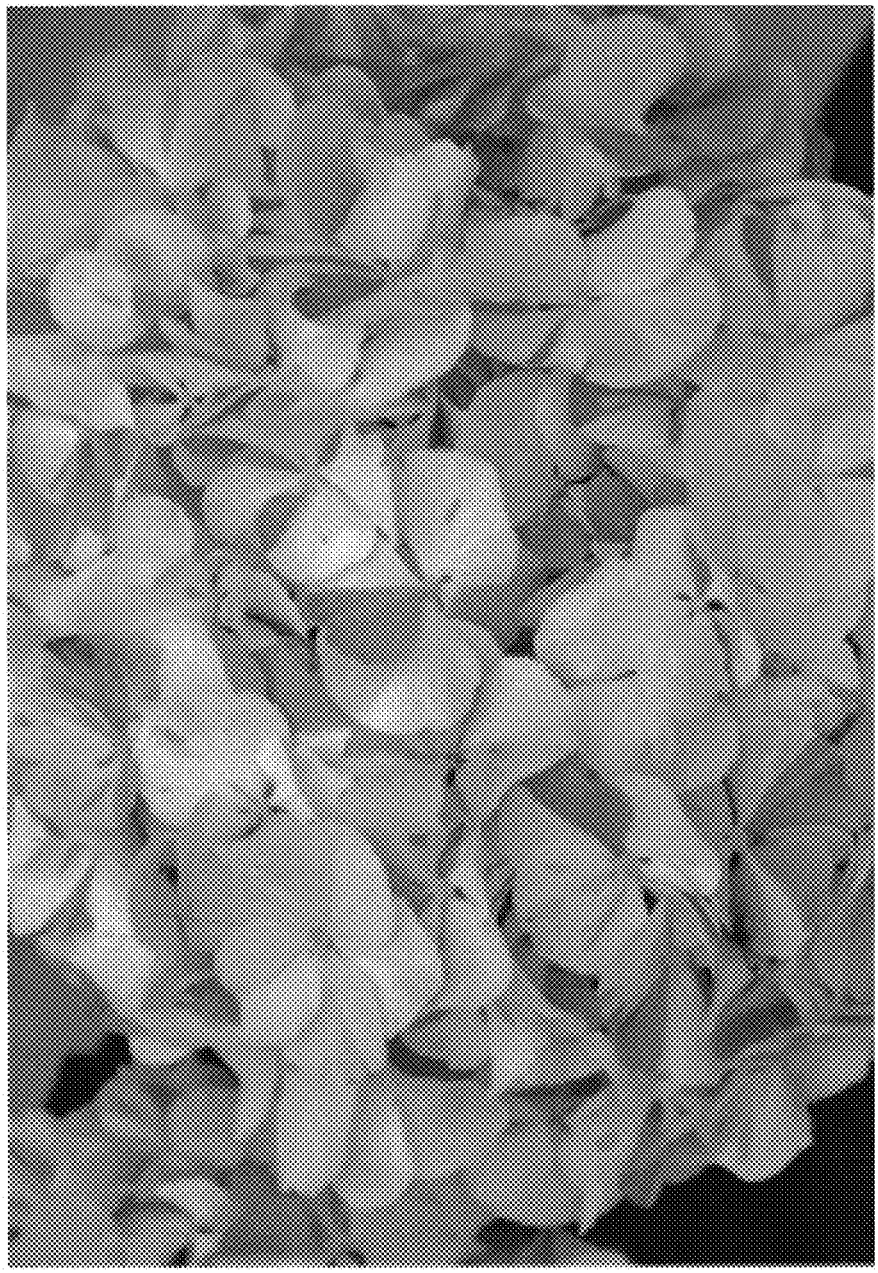

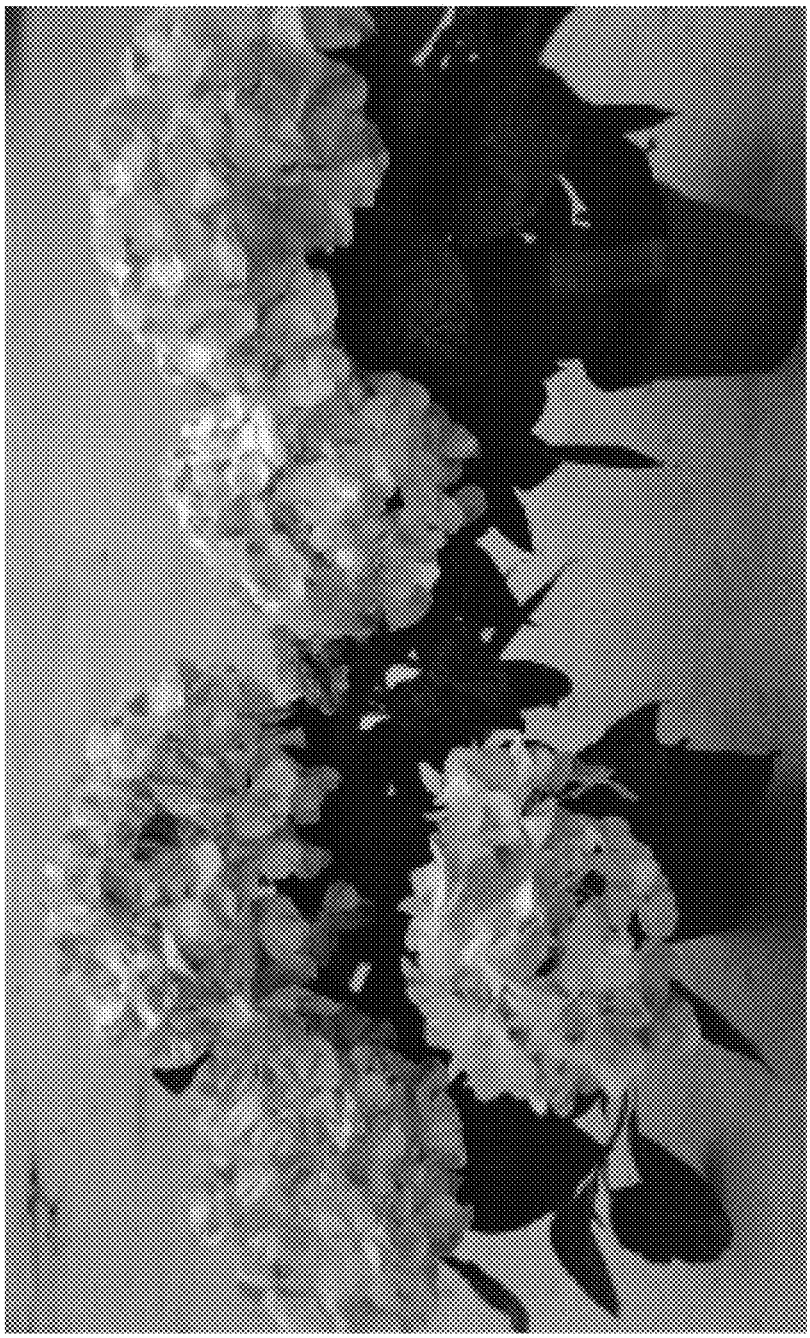

* * * * *